United States Patent [19]

Ringlien

[11] Patent Number: 5,243,400
[45] Date of Patent: Sep. 7, 1993

[54] INSPECTION OF TRANSPARENT CONTAINERS

[75] Inventor: James A. Ringlien, Maumee, Ohio

[73] Assignee: Owens-Brockway Glass Container Inc., Toledo, Ohio

[21] Appl. No.: 874,484

[22] Filed: Apr. 27, 1992

[51] Int. Cl.$^5$ ............................................. G01N 21/41
[52] U.S. Cl. .................................. 356/240; 250/223 B; 356/428
[58] Field of Search ............... 356/239, 240, 128, 428; 250/223 B

[56] References Cited

U.S. PATENT DOCUMENTS

| | | | |
|---|---|---|---|
| 2,708,857 | 5/1955 | Golding | 356/239 |
| 3,454,759 | 7/1969 | Calhoun . | |
| 3,478,218 | 11/1969 | Wuellner et al. | 356/239 |
| 3,943,278 | 3/1976 | Ramsey, Jr. . | |
| 3,952,150 | 4/1976 | Gerardin et al. . | |
| 4,376,951 | 3/1983 | Miyazawa | 356/240 |
| 4,487,322 | 12/1984 | Juvinall | 356/240 |
| 4,547,067 | 10/1985 | Watanabe | 356/239 |
| 4,601,395 | 7/1986 | Juvinall et al. | 356/240 |
| 4,606,634 | 8/1986 | Bieringer | 356/240 |
| 4,610,542 | 9/1986 | Ringlien | 250/223 B |
| 4,697,076 | 9/1987 | Yoshida | 356/240 |
| 4,924,083 | 5/1990 | Ishikawa et al. | 356/240 |
| 5,004,909 | 4/1991 | Fukuchi | 356/240 |

FOREIGN PATENT DOCUMENTS 63-149547 12/1986 Japan .

Primary Examiner—Richard A. Rosenberger

[57] ABSTRACT

Apparatus for detecting commercial variations in transparent containers such as glass bottles that comprises a light source for directing diffused light energy through a container under inspection. A light sensing camera is positioned to receive an image of the light source transmitted through the container sidewall. A light control film is positioned adjacent to the light source between the light source and the container, and comprises a plurality of parallel slats spaced from each other so as to limit the angle from which the image of the light source can be viewed at the camera. Commercial variations are detected as a function of variations in light intensity received at the camera. In the preferred embodiment of the invention, first and second arrays of spaced parallel slats are positioned adjacent to the light source, with the slats of the first array being at an angle to the slats of the second array so as to project a moiré fringe pattern through the container onto the camera.

12 Claims, 3 Drawing Sheets

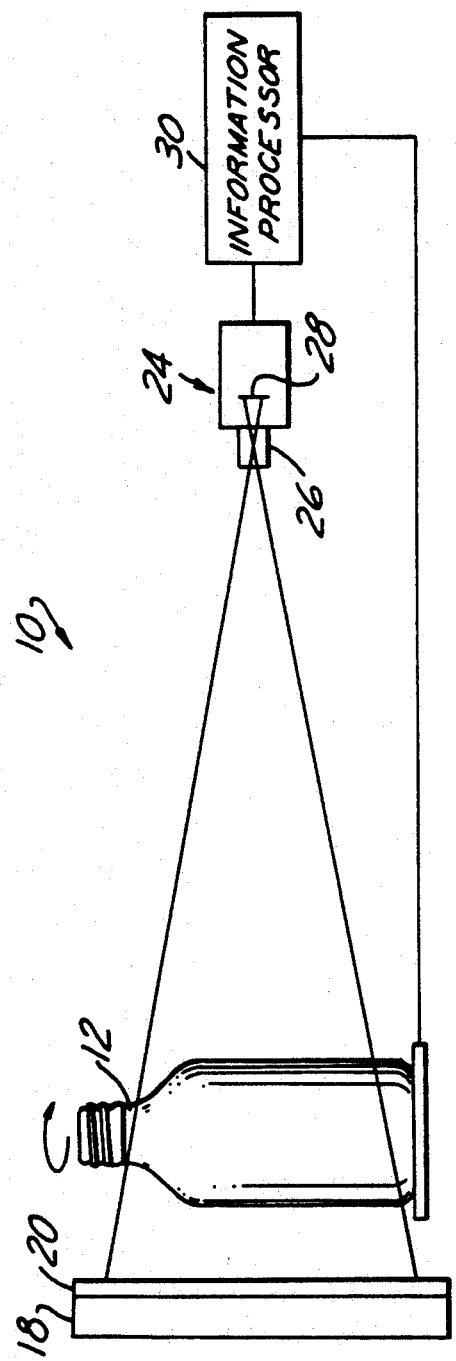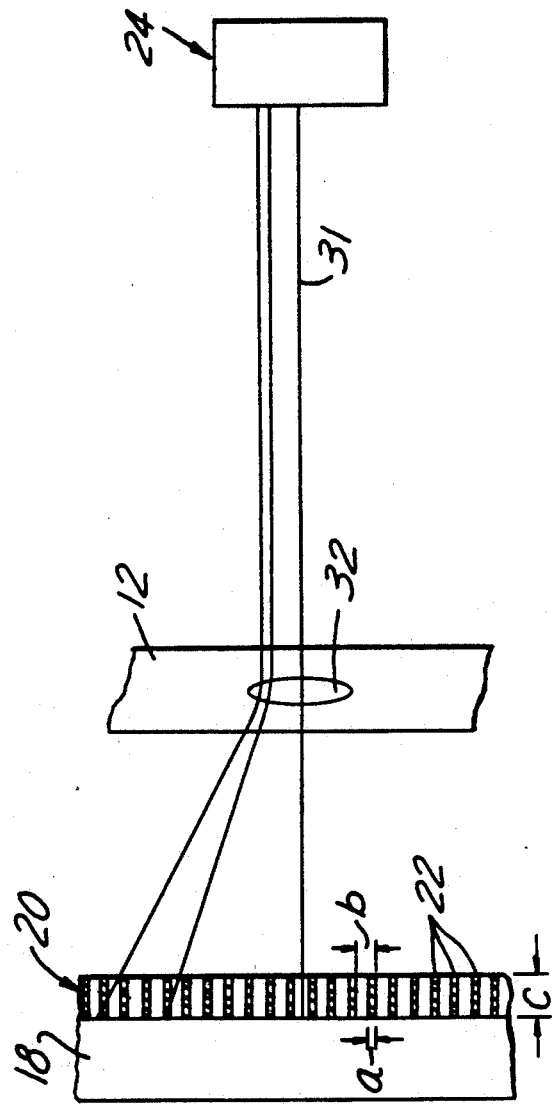
FIG. 1
FIG. 2

INSPECTION OF TRANSPARENT CONTAINERS

The present invention is directed to inspection of transparent containers for commercial variations or defects that affect optical properties of the sidewalls of the containers, and more particularly to an apparatus and method for enhanced detection of refractive variations.

BACKGROUND AND OBJECTS OF THE INVENTION

In the manufacture of transparent containers such as glass bottles, various types of checks or defects may occur in the sidewalls of the containers. These checks or defects, termed "commercial variations" in the art, can affect commercial acceptability of the containers. The commercial variations may be opaque, such as stones, or may be refractive such as blisters, bubbles or tears.

It has heretofore been proposed to employ electro-optical inspection systems for detecting commercial variations that affect optical properties of the containers. The basic principle is that a light source is positioned on one side of the container and a camera is positioned on the other. The light source may be configured to have an intensity that varies across one dimension of the source. Light rays normally travel from the source straight through the container sidewall and are then focused onto the camera, and are viewed at the camera at a given intensity. However, a refractive commercial variation bends the light ray as it travels through the container sidewall, so that the image projected onto the camera is of a different area of the light source. If such different area has a different intensity than the area normally imaged onto the camera, the camera can detect the refractive sidewall defect.

U.S. Pat. No. 4,610,542 discloses one technique for varying the effective intensity of the light source across the light source. An elongated filament lamp is positioned along the upper edge of a diffuser plate to produce an intensity gradient in the vertical direction across the light source. The upper area of the diffuser plate is brightest, the middle area has average brightness and the lower area is darkest. U.S. Pat. No. 4,601,395 discloses another technique in which a filter is placed across the light source diffuser screen to provide differing areas of effective light source intensity.

Although the systems disclosed in the noted patents, both of which are assigned to the assignee hereof, address problems theretofore extant in the art, further improvements remain desirable. In particular, it is desirable to provide a larger area of contrast associated with refractive commercial variations so as to enhance the probability of detecting relatively small variations such as bird swings, enlargements or mounds that surround small stones, and settle waves that frequently occur in blow-and-blow glassware manufacturing processes. It is a general object of the present invention to provide an inspection apparatus and method that accomplish this objective. Another object of the present invention is to provide an apparatus and method for inspecting transparent containers of the type described above in which the filter mechanism placed across the light source for creating the light source intensity gradient is of inexpensive manufacture.

SUMMARY OF THE INVENTION

Apparatus for detecting commercial variations in transparent containers such as glass bottles in accordance with a presently preferred embodiment of the invention comprises a light source for directing diffused light energy through a container under inspection. A light sensing camera is positioned to receive an image of the light source transmitted through the container sidewall. A light control film is positioned adjacent to the light source between the light source and the container, and comprises a plurality of parallel slats spaced from each other so as to limit the angle from which the image of the light source can be viewed at the camera. Commercial variations are detected as a function of variations in light intensity received at the camera. In the preferred embodiment of the invention, first and second arrays of spaced parallel slats are positioned adjacent to the light source, with the slats of the first array being at an angle to the slats of the second array so as to project a moiré fringe pattern through the container onto the camera.

In accordance with one aspect of the invention, the camera is positioned opposite the light source at an orientation to view the light source through the container on a line of sight along an axis parallel to the slats. Any refractive variation in the container sidewall refracts or bends the line of sight at an angle to said axis. As this angle increases, the slats progressively obstruct the light source, until the camera can no longer see the light source at the critical viewing angle of the slats.

In accordance with another aspect of the invention, a moiré fringe pattern is projected onto the container, and the container sidewall is moved in a direction or orthogonal to the pattern, preferably by rotating the container about its central axis. In this way, any refractive variations in the container sidewall refract line of sight of the camera from its axis to sweep through alternating light and dark areas of the fringe pattern. Refractive variations may thereby be detected as a function of such varying light intensity incident on the camera.

BRIEF DESCRIPTION OF THE DRAWINGS

The invention, together with additional objects, features and advantages thereof, will be best understood from the following description, the appended claims and the accompanying drawings in which:

FIG. 1 is an electro-optical schematic diagram that illustrates one presently preferred embodiment of the invention;

FIG. 2 is an enlargement of a portion of FIG. 1 that illustrates operation of the invention;

DETAILED DESCRIPTION OF PREFERRED EMBODIMENTS

Figure 3:
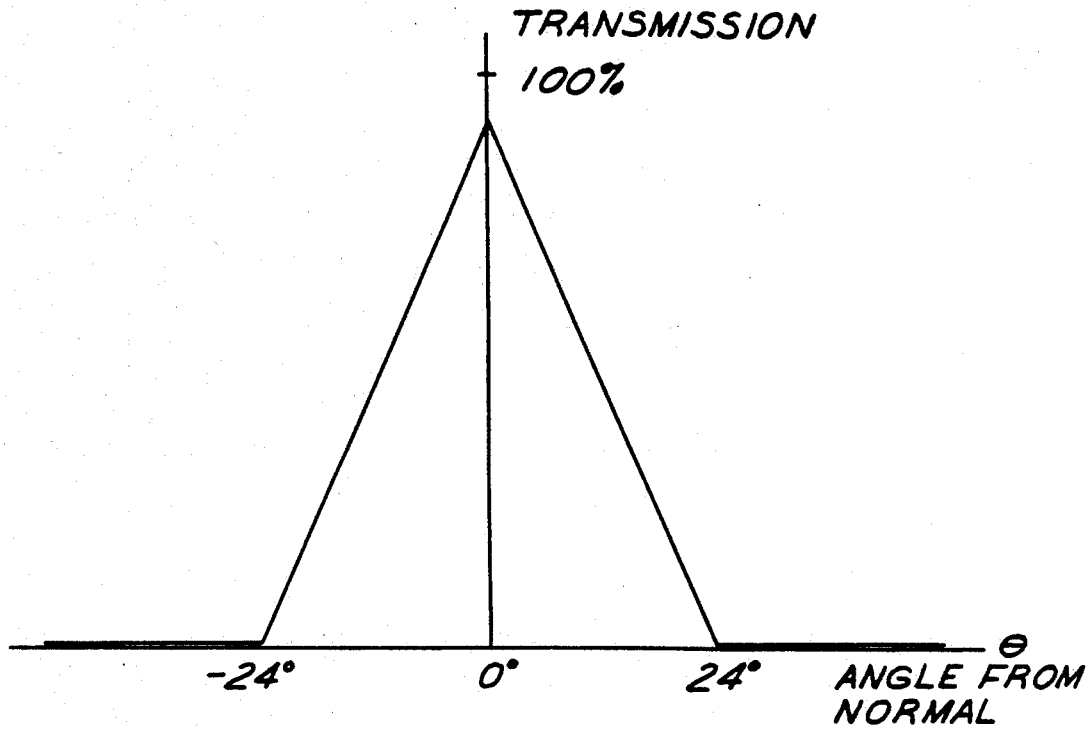
FIG. 3 is a graph that illustrates intensity gradient across the light source as a function of viewing angle in the embodiments of FIGS. 1 and 2.

FIG. 1 illustrates apparatus 10 for inspecting transparent containers 12 for commercial variations that affect the optical properties of the container sidewalls. Apparatus 10 includes a light source 14 in the form of one or more light bulbs 16 positioned on one side of a diffuser screen or plate 18. A light control film 20 is positioned adjacent to diffuser screen 18 between screen 18 and container 12. As shown in the enlargement of FIG. 2, light control film 20 comprises a plurality of closely spaced parallel slats 22 having an elongated dimension that extends in the horizontal direction and a lateral dimension that extends outwardly from diffuser screen 18. Slats 22 are longitudinally and laterally parallel with each other, and are spaced from each other by uniform vertical increments.

A camera 24 is positioned on the opposing side of container 12, and includes a lens 26 for projecting an image of light source 14 transmitted through container 12 onto a light sensing element 28 within the camera. In the preferred embodiments of the invention, light sensing element 28 takes the form of a linear array sensor (FIG. 3) having a plurality of light sensing elements 29 disposed in a vertical array parallel to and optically aligned with the axis of container 12. An information processor 30 is coupled to camera 24 and to container 12 for scanning elements 29 of camera array 28 at increments of container rotation about its central axis, and thereby obtaining a two-dimensional image of the container sidewall and of light source 14 as viewed through the container sidewall.

Figure 4:
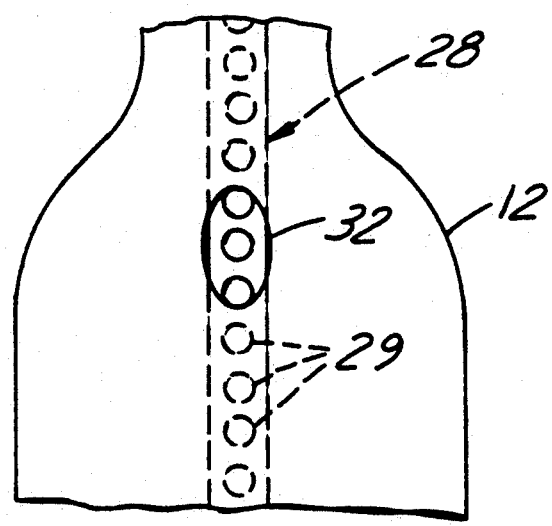
FIG. 4 is a fragmentary schematic diagram that illustrates effect of a refractive variation on the image received by the camera in the embodiment of FIGS. 1-2.

Operation of the closely spaced horizontal slats 22 of light control film 20 is akin to operation of venetian blinds disposed in horizontal position adjacent to a building window. When viewing the window and building exterior straight through the blinds, the blinds present little obstruction. However, as the viewing position or angle changes in the vertical direction, the blinds effectively obstruct the view through the window. Thus, as shown in FIGS. 2-4, when the camera line of sight is straight through the sidewall of container 12 without obstruction, or straight through the center of a blister 32 illustrated in FIG. 2, the camera effectively sees diffuser screen 18 without alteration of light intensity. However, as the camera line of sight is effectively bent by the refractive effects at the upper (and lower) edges of blister 32, the camera line of sight sees progressively less light through the refracting region. Eventually the viewing angle exceeds the allowable viewing angle of control film 20, so that the camera then essentially receives a dark image. The more the camera's line of sight is deflected, the darker the refractive region appears. In other words, the darkness or grayness the camera sees is proportional to refraction angle or glass wedge at the defect. Thus, in FIG. 4, the image of blister 32 has dark upper and lower edges due to this phenomenon. Information processor 30 can detect these variation-induced effects employing the techniques disclosed in U.S. Pat. No. 4,601,395 discussed above.

FIG. 3 illustrates light intensity versus viewing angle from a line 31 (FIG. 2) normal to the light source. Transmission is essentially unobstructed along line of sight axis 31 normal to the light source, and is progressively attenuated linearly up to the critical viewing angle of the control film, beyond which the control film is effectively opaque. In one presently preferred implementation of the invention, the slats 22 of screen 20 are of lateral dimension and vertical spacing with respect to each other as to obtain a critical angle of 48° (plus and minus 24°) as shown in FIG. 3. Suitable light control film of this character may be obtained from 3M Corporation, No. LCF-P ABRO O OB4B. This film has dimensions a, b, c (FIG. 2) of 0.001 inch, 0.005 inch and 0.020 inch respectively, 3M also markets film having 60° and 90° cutoff angles.

The invention illustrated in FIGS. 1-4 thus provides enhanced detection of refractive defects such as blisters 32, bird swings and settle waves. Small stones are typically difficult to detect in electro-optical inspection systems because they appear as a very small dark spot against a bright background. However, the present invention provides enhanced detection of small stones by enabling the camera to detect the bulge or mound of glass that typically surrounds a stone as a refractive commercial variation.

Figure 5:
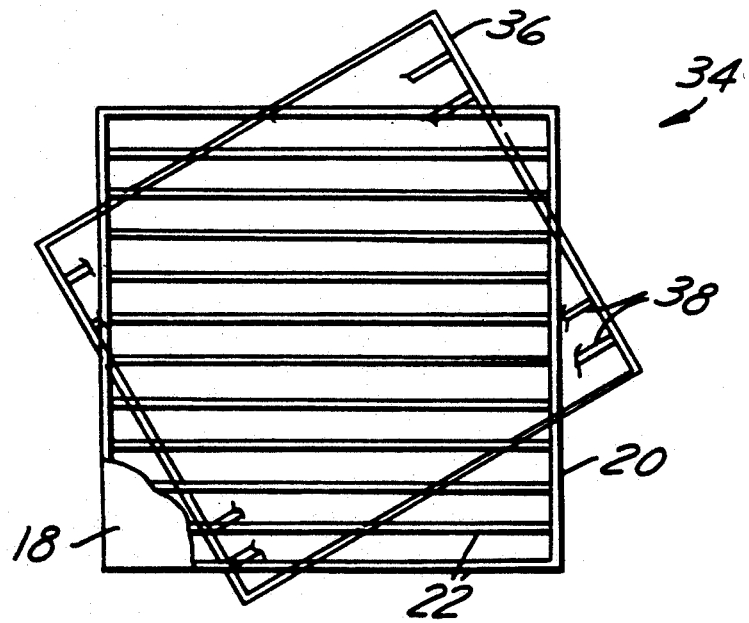
FIG. 5 is a fragmentary schematic diagram that illustrates a modified embodiment of the invention.
Figure 6:
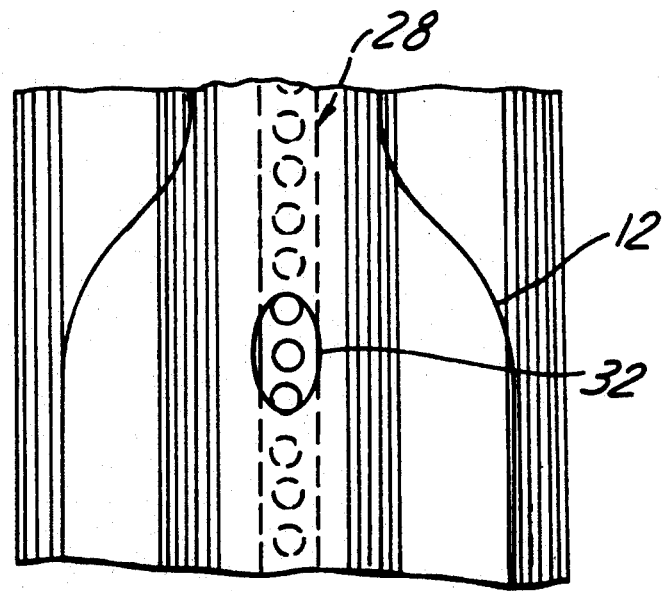
FIG. 6 is a fragmentary schematic diagram that illustrates the effect of a refractive variation on the image received by the camera in the embodiment of FIG. 5.

FIG. 5 illustrates a light source 34 in a modified and presently preferred implementation of the invention. A pair of essentially identical light control films 20, 36 are placed over the diffuser plate 18 between plate 18 and container 12 (as shown in FIG. 1). The two light films 20, 36 have slats 22, 38 at a slight angle to each other so as to create a vertical moiré fringe pattern at the container. The angle between slats 22, 38 is exaggerated in FIG. 4 for purposes of illustration, and would typically be on the order of 2°. The moiré fringe pattern is illustrated in FIG. 6 as alternating light and dark vertical bands. As a refractive defect passes through the camera field of view (FIG. 6), either by rotating the container or moving the container horizontally past the camera, the camera line of sight is bent horizontally by the refractive defect so as to sweep the vertical fringe pattern, thereby creating a series of high and low intensity signals at the camera. Such alternating signals may be readily detected at camera 24 and information processor 30 in the manner described in U.S. Pat. No. 4,601,395 discussed above. In addition to producing the moiré fringe pattern, the two control film layers further restrict the emission angles of light from the diffuse light source in the vertical direction. This increases sensitivity of the method to defects that might refract the camera line of sight by similar angles.

I claim:

1. Apparatus for detecting commercial variations in transparent containers comprising:

a light source for directing diffused illumination through a container under inspection, light sensing means positioned to receive an image of said light source transmitted through the container, means positioned adjacent to said light source between said light source and the container comprising a plurality of parallel slats spaced from each other so as to limit the angle from which the image of said light source can be viewed at said light sensing means, and means for detecting commercial variations in the container as a function of variations of light intensity received at said sensing means.

2. The apparatus set forth in claim 1 wherein said means positioned adjacent to said light source comprises first and second arrays of said spaced parallel slats, slats of said first array being at an angle to slats of said second array so as to project a moiré fringe pattern through the container onto said sensing means.

3. The apparatus set forth in claim 1 wherein said slats have a longitudinal dimension at horizontal orientation.

4. The apparatus set forth in claim 1 wherein said slats have a lateral dimension between said light source and said camera that is coordinated with spacing between said slats to limit said angle to 48°.

5. The apparatus set forth in claim 1 wherein said light source includes a diffuser on a side of said slats remote from the container.

6. A method of inspecting transparent containers for refractive variations in the sidewalls thereof, comprising the steps of:
   (a) directing a source of diffused illumination onto the container through a plurality of closely spaced parallel slats,
   (b) positioning a camera on a side of container opposite to said source at an orientation to view said source through the container along an axis parallel to said slats such that any refractive variations in the sidewall of the container refract line of sight of said camera to an angle to said axis, and
   (c) detecting commercial variations in the sidewall of the container as a function of intensity of light energy incident on said camera from said source through said slats.

7. The method set forth in claim 6 comprises the additional step of:
   (d) moving the container sidewall relative to said axis in a direction perpendicular to said axis.

8. The method set forth in claim 7 wherein said step (d) comprises the step of rotating the container.

9. The method set forth in claim 7 wherein said step (d) comprises the step of moving the container sidewall in a direction parallel to said slats.

10. A method of inspecting transparent containers for refractive commercial variations in the sidewalls thereof, comprising the steps of:
    (a) projecting a moiré fringe pattern onto a container,
    (b) positioning a camera on a side of the container to view the container along an axis perpendicular to said fringe pattern,
    (c) moving the sidewall of the container in a direction perpendicular to said fringe pattern and to said axis such that any refractive variations in the sidewall of the container refract line of sight of said camera from said axis and sweep through alternating light and dark areas of said fringe pattern, and
    (d) detecting any such refractive variations in the container sidewall as a function of varying intensity of light incident on said camera as said line of sight sweeps said pattern.

11. The method set forth in claim 10 wherein said fringe pattern is vertical.

12. The method set forth in claim 10 wherein said step (c) is carried out by rotating the container about its axis.

* * * * *